(12) United States Patent
Ferguson et al.

(10) Patent No.: US 11,560,658 B2
(45) Date of Patent: Jan. 24, 2023

(54) METHOD OF MAKING A NONWOVEN WEB

(71) Applicant: Kimberly-Clark Worldwide, Inc., Neenah, WI (US)

(72) Inventors: Timothy D. Ferguson, Alpharetta, GA (US); David A. Palzewicz, Canton, GA (US); Daniel M. Nussbaum, Neenah, WI (US); Tom R. Belau, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 125 days.

(21) Appl. No.: 16/639,063

(22) PCT Filed: Aug. 16, 2018

(86) PCT No.: PCT/US2018/000240
§ 371 (c)(1),
(2) Date: Feb. 13, 2020

(87) PCT Pub. No.: WO2019/035965
PCT Pub. Date: Feb. 21, 2019

(65) Prior Publication Data
US 2020/0224346 A1    Jul. 16, 2020

Related U.S. Application Data

(60) Provisional application No. 62/546,408, filed on Aug. 16, 2017.

(51) Int. Cl.
*B29C 55/08*    (2006.01)
*D04H 3/08*    (2006.01)
(Continued)

(52) U.S. Cl.
CPC .............. *D04H 3/14* (2013.01); *B29C 55/005* (2013.01); *B29C 55/146* (2013.01); *D02J 1/228* (2013.01);
(Continued)

(58) Field of Classification Search
CPC ..... B29C 55/005; B29C 55/08; B29C 55/146; D01D 5/16; D02J 1/22; D02J 1/228;
(Continued)

(56) References Cited

U.S. PATENT DOCUMENTS

| 4,668,566 A | 5/1987 | Braun |
| 4,978,486 A | 12/1990 | Ito et al. |

(Continued)

FOREIGN PATENT DOCUMENTS

| CN | 104138311 A | 11/2014 |
| EP | 000461710-0001 | 11/2006 |

(Continued)

OTHER PUBLICATIONS

Zhejiang Huachen Nonwovens Co., Ltd., "100% PP Non Woven Fabric Baby Diaper Raw Material for Diaper Caddy", Jul. 30, 2017, https://zjhuachen.en.alibaba.com/product/60233744329-802033989/100_PP_Non_Woven_Fabric_Baby_Diaper_Raw_Material_for_Diaper_Caddy.html?spm=a2700.8304367.prewdfa4cf.10.68706ea4vNdEMR.

(Continued)

*Primary Examiner* — Leo B Tentoni

(57) ABSTRACT

Soft point bonded nonwoven webs, and methods of making the same, are described that utilize a pattern of small, discrete bond points in a sequent pattern that together form macro-elements. The macro-elements are themselves positioned and aligned within a pattern such that mechanical stretching operations on the point bonded nonwoven webs (Continued)

yields soft and bulky fabrics but with reduced incidence of tearing or rupturing of the individual bond points.

13 Claims, 13 Drawing Sheets

(51) Int. Cl.
*D06C 3/00* (2006.01)
*D06C 3/02* (2006.01)
*D04H 3/14* (2012.01)
*D04H 3/007* (2012.01)
*D06C 3/06* (2006.01)
*B29C 55/00* (2006.01)
*B29C 55/14* (2006.01)
*D02J 1/22* (2006.01)

(52) U.S. Cl.
CPC .............. *D04H 3/007* (2013.01); *D06C 3/021* (2013.01); *D06C 3/06* (2013.01)

(58) Field of Classification Search
CPC ... D04H 3/08; D04H 3/16; D06C 3/00; D06C 3/02; D06C 3/021; D06C 3/06
USPC .......... 264/210.1, 210.7, 288.4, 289.3, 290.2
See application file for complete search history.

(56) References Cited

U.S. PATENT DOCUMENTS

| | | | |
|---|---|---|---|
| 5,370,764 A | 12/1994 | Alikhan | |
| 5,490,902 A | 2/1996 | Schulz | |
| 5,514,470 A | 5/1996 | Haffner et al. | |
| 5,562,805 A | 10/1996 | Kamps et al. | |
| 5,626,571 A | 5/1997 | Young et al. | |
| 5,628,097 A | 5/1997 | Benson et al. | |
| 5,810,954 A | 9/1998 | Jacobs et al. | |
| 5,814,390 A | 9/1998 | Stokes et al. | |
| 5,817,394 A | 10/1998 | Alikhan et al. | |
| D403,763 S | 1/1999 | Lynard et al. | |
| D403,764 S | 1/1999 | Lynard et al. | |
| 5,879,780 A | 3/1999 | Kindinger et al. | |
| 5,883,028 A | 3/1999 | Morman et al. | |
| 5,914,084 A | 6/1999 | Benson et al. | |
| D426,889 S | 6/2000 | Bissah et al. | |
| 6,093,665 A | 7/2000 | Sayovitz et al. | |
| 6,096,668 A | 8/2000 | Abuto et al. | |
| D430,665 S | 9/2000 | Kirkbride et al. | |
| 6,129,801 A | 10/2000 | Benson et al. | |
| D434,849 S | 12/2000 | Kirkbride et al. | |
| 6,176,954 B1 | 1/2001 | Tsuji et al. | |
| 6,203,654 B1 | 3/2001 | McFall et al. | |
| D443,766 S | 6/2001 | Bredendick et al. | |
| D448,078 S | 9/2001 | Deoliveira et al. | |
| D448,478 S | 9/2001 | Deoliveira et al. | |
| D456,899 S | 5/2002 | Levy et al. | |
| 6,383,431 B1 | 5/2002 | Dobrin et al. | |
| D461,893 S | 8/2002 | Gannon et al. | |
| D463,548 S | 9/2002 | Gannon et al. | |
| D463,549 S | 9/2002 | Gannon et al. | |
| 6,506,329 B1 | 1/2003 | Curro et al. | |
| D478,661 S | 8/2003 | Levy et al. | |
| 6,605,172 B1 | 8/2003 | Anderson et al. | |
| 6,610,390 B1 | 8/2003 | Kauschke et al. | |
| 6,620,485 B1 | 9/2003 | Benson et al. | |
| D485,353 S | 1/2004 | Miller et al. | |
| 6,726,870 B1 | 4/2004 | Benson et al. | |
| 6,729,869 B2 | 5/2004 | Lofink | |
| 6,733,626 B2 | 5/2004 | Ruthven et al. | |
| 6,896,767 B2 | 5/2005 | Wilhelm | |
| D506,255 S | 6/2005 | Drzewiecki et al. | |
| 6,909,028 B1 | 6/2005 | Shawver et al. | |
| D508,993 S | 8/2005 | Drzewiecki et al. | |
| D512,505 S | 12/2005 | Vinson | |
| 6,994,763 B2 | 2/2006 | Austin | |
| 7,056,404 B2 | 6/2006 | McFall et al. | |
| 7,198,742 B2 | 4/2007 | Gerndt | |
| 7,252,870 B2 | 8/2007 | Anderson et al. | |
| 7,410,683 B2 | 8/2008 | Curro et al. | |
| D594,972 S | 6/2009 | Cauwood et al. | |
| D594,973 S | 6/2009 | Francoeur | |
| D594,974 S | 6/2009 | Liu et al. | |
| D594,975 S | 6/2009 | Desautels et al. | |
| D594,976 S | 6/2009 | Gubernick | |
| D594,977 S | 6/2009 | Jackson et al. | |
| D594,978 S | 6/2009 | Cauwood et al. | |
| D594,979 S | 6/2009 | Desautels et al. | |
| 7,740,786 B2 | 6/2010 | Gerndt et al. | |
| D625,408 S | 10/2010 | Cerbelli et al. | |
| 7,811,271 B2 | 10/2010 | Digiacomantonio et al. | |
| 7,971,526 B2 | 7/2011 | Blenke et al. | |
| 8,062,572 B2 | 11/2011 | Qureshi et al. | |
| D657,958 S | 4/2012 | Ehrman et al. | |
| 8,231,377 B2 | 7/2012 | Wittner et al. | |
| 8,236,121 B2 | 8/2012 | Ashraf | |
| 8,387,497 B2 | 3/2013 | Raidel et al. | |
| D686,734 S | 7/2013 | Tsuruta et al. | |
| D693,922 S | 11/2013 | Frias et al. | |
| D694,892 S | 12/2013 | Chan et al. | |
| D697,216 S | 1/2014 | Chan et al. | |
| 8,647,553 B2 | 2/2014 | Kobayashi et al. | |
| 8,704,036 B2 | 4/2014 | Hammons et al. | |
| 8,722,963 B2 | 5/2014 | Kanya et al. | |
| D708,751 S | 7/2014 | Chan et al. | |
| 8,907,156 B2 | 12/2014 | Roe et al. | |
| 8,945,452 B2 | 2/2015 | Morita et al. | |
| 9,011,625 B2 | 4/2015 | Siqueira et al. | |
| 9,028,652 B2 | 5/2015 | Curro et al. | |
| 9,034,230 B2 | 5/2015 | Qureshi et al. | |
| 9,044,353 B2 | 6/2015 | Stone et al. | |
| 9,050,777 B2 | 6/2015 | Kauschke et al. | |
| D745,689 S | 12/2015 | Chan et al. | |
| 9,358,705 B2 | 6/2016 | Zhao et al. | |
| 9,415,538 B2 | 8/2016 | Mullane | |
| D765,993 S | 9/2016 | Palzewicz | |
| 9,452,089 B2 | 9/2016 | Marinelli et al. | |
| 9,468,563 B2 | 10/2016 | Coe et al. | |
| 9,534,325 B2 | 1/2017 | Orr et al. | |
| 9,550,309 B2 | 1/2017 | Gibson et al. | |
| D779,655 S | 2/2017 | Brown et al. | |
| D779,656 S | 2/2017 | Fites et al. | |
| D779,659 S | 2/2017 | Fites et al. | |
| D780,911 S | 3/2017 | Fites et al. | |
| 9,604,429 B2 | 3/2017 | Borchardt et al. | |
| 2002/0119720 A1* | 8/2002 | Arora | A61F 13/51466 442/361 |
| 2002/0150609 A1* | 10/2002 | Kono | B32B 3/28 424/443 |
| 2003/0228822 A1 | 12/2003 | Pereira et al. | |
| 2005/0064136 A1 | 3/2005 | Turner et al. | |
| 2005/0245162 A1 | 11/2005 | McCormack et al. | |
| 2006/0063454 A1 | 3/2006 | Chung et al. | |
| 2006/0073755 A1* | 4/2006 | George | D04H 3/16 442/352 |
| 2006/0141888 A1 | 6/2006 | Morman | |
| 2007/0219523 A1 | 9/2007 | Bruun et al. | |
| 2008/0070463 A1 | 3/2008 | Arora et al. | |
| 2009/0294044 A1 | 12/2009 | Gill et al. | |
| 2010/0032867 A1 | 2/2010 | Schmidt | |
| 2012/0277393 A1 | 11/2012 | Curro et al. | |
| 2012/0315440 A1 | 12/2012 | Ichikawa et al. | |
| 2013/0288013 A1 | 10/2013 | Jones et al. | |
| 2014/0039434 A1 | 2/2014 | Xu et al. | |
| 2014/0072767 A1 | 3/2014 | Klaska et al. | |
| 2014/0088535 A1 | 3/2014 | Xu et al. | |
| 2014/0117135 A1 | 5/2014 | Graff et al. | |
| 2014/0276517 A1 | 9/2014 | Chester et al. | |
| 2014/0324009 A1 | 10/2014 | Lee et al. | |
| 2015/0164705 A1 | 6/2015 | Thomas et al. | |
| 2015/0173964 A1 | 6/2015 | Coe et al. | |
| 2015/0174857 A1* | 6/2015 | Schmitz | A61F 13/15634 156/146 |
| 2016/0235590 A1 | 8/2016 | Coe et al. | |

(56) References Cited

U.S. PATENT DOCUMENTS

2016/0235592 A1    8/2016  Coe et al.
2016/0362825 A1*  12/2016  Novarino ............... D04H 1/559
2017/0000660 A1    1/2017  Wade et al.

FOREIGN PATENT DOCUMENTS

| EP | 1071849 B2 | 2/2007 |
| EP | 1902168 B1 | 7/2010 |
| EP | 2096201 B1 | 6/2015 |
| WO | 9805813 A1 | 2/1998 |
| WO | 9937841 A1 | 7/1999 |
| WO | 08129138 A1 | 10/2008 |
| WO | 14044235 A1 | 3/2014 |
| WO | 16172929 A1 | 11/2016 |

OTHER PUBLICATIONS

Quanzhou Niso Industry Co., Ltd., "Super Soft 3D Dotted Embossing Nonwoven Fabric for Diaper/Sanitary Napkin Top sheet", Jul. 30, 2017, http://www.qzniso.com/super-soft-dotted-3d-embossing-nonwoven-for-diaper-raw-materials_p985.html.
Guangzhou Yamaza Sanitary Products Co., Ltd., "Super Soft Nonwoven Fabric Ultra Thick Cloth Baby Diaper Punishment/baby comfortable diapers", Jul. 30, 2017, https://www.alibaba.com/product-detail/Super-Soft-Non-woven-Fabric-Ultra_60659235865.html.

* cited by examiner

METHOD OF MAKING A NONWOVEN WEB

This application claims priority from U.S. provisional Patent Application Ser. No. 62/546,408 filed on Aug. 16, 2017, the entire contents of which are incorporated herein by reference.

BACKGROUND

Nonwoven fabrics are commonly used in a variety of disposable products such as diapers, panty-liners, baby wipes and other personal hygiene products. Due to their low cost and strength, nonwoven materials are utilized in a wide variety of different components in such products. In one aspect, many of the functional materials used in personal care products, e.g. elastic materials and barrier films, lack the desired softness attributes and have an unpleasant hand-feel. Thus, it is common to use nonwoven materials as a facing layer together with other functional layers to improve the overall hand-feel and softness of the laminate. For example, liquid impermeable outer covers used in absorbent personal care articles often comprise a laminate including a barrier film, such as a microporous film, bonded to a polypropylene spunbond fiber nonwoven web. However, while nonwovens generally have a hand-feel that is better than various functional materials, many nonwoven webs still can be relatively rigid in nature and/or lack the level of softness consumer's desire. For these reasons, various attempts have been made to improve the softness of nonwoven webs through the addition of additives as well as through mechanical treatments. For example, one technique that has been employed is stretching of the nonwoven fabrics via inter-meshing grooved rolls, commonly referred to as ring-rolling or incremental stretching. Such treatments have provided some improvement with regard to the overall hand feel of the nonwoven. However, such treatments can lead to increased fuzzing or linting as well as the formation of tears within the nonwoven. Often such linting or tearing may be on a limited scale or size, nevertheless the formation of such irregularities detracts from the overall perception of quality and can erode a consumer's confidence in the ability of the product to perform its intended function. For example, where a nonwoven web is used as an outer facing material of a liquid impermeable outer cover for a diaper, even though small tears may not materially impact the barrier function of the film/nonwoven laminate, such tears can cause the consumer to question the ability of the product to properly perform.

Therefore, in order to address the continued desire for nonwoven webs with still greater levels of softness and/or hand-feel, the present invention provides nonwoven fabrics having a unique and improved combination of properties, namely pleasing hand and softness together with high strength and greatly reduced incident of visual defects. In this regard, the patterns and processes of the present invention are significantly better able to withstand the forces and stresses commonly associated with post-formation mechanical softening treatments.

SUMMARY

Generally speaking, nonwoven webs having one or more improved properties as noted above, can be achieved by employing a particular bond pattern in combination with one or more mechanical stretching operations. In certain embodiments, the bond pattern may comprise (i) discrete individual bond points having a maximum dimension of 1.25 mm or less and an aspect ratio less than 3:1, (ii) macro-elements formed by the individual bond points in a sequent pattern and wherein the macro-elements extend substantially in the machine-direction and have a machine-direction length between about 4 and about 25 mm, (iii) unbonded pockets adjacent the macro-elements having an area between about 20 and about 50 $mm^2$, and (iv) an overall bond area of between about 5% and about 20%. After imparting the bond pattern to the nonwoven web, a first stretching force is applied to the pattern bonded nonwoven web to increase one or more of the webs dimensions and form soft, high-loft regions. For example, the pattern bonded nonwoven web may be stretched in the cross-direction thereby increasing its dimension in the cross direction, i.e. increasing its width. Optionally, the method may further comprise applying a second stretching force to the pattern bonded nonwoven web to increase the same or a different dimension of the pattern bonded nonwoven web. For example, the nonwoven web may be stretched in the machine direction whereby the pattern bonded nonwoven elongates in the machine direction and necks, i.e. the CD dimension or width decreases. Despite the strong forces applied by the one or more mechanical stretching operations, the resulting nonwoven web will have tears within less than 1%, or even less than 0.1%, of the individual bond points.

In an alternate embodiment, the bond pattern may comprise (i) discrete individual bond points having a maximum dimension of 1.25 mm or less, (ii) macro-elements formed by the individual bond points in a sequent pattern, (iii) an overall density of macro-elements of between about 1 and about 5 per square centimeter, and (iv) an overall bond area of between about 5% and about 20%. In still other embodiments, the macro-elements may be positioned in a plurality of rows extending substantially in the cross direction and wherein adjacent rows are staggered such that macro-elements of an upper row overlay unbonded pockets of the underlying row. In certain embodiments, the spacing between individual bond points forming the macro-elements is between 0.03 and about 0.7 mm and the spacing between macro-elements is between about 0.9 mm and about 2.5 mm. Further, the rows may overlap in the cross direction. In addition, suitable bond patterns may employ macro-elements having a CD width of between about 1 and about 7 mm and/or a machine-direction length between about 4 and about 25 mm.

FIGURES

DEFINITIONS

Figure 1:
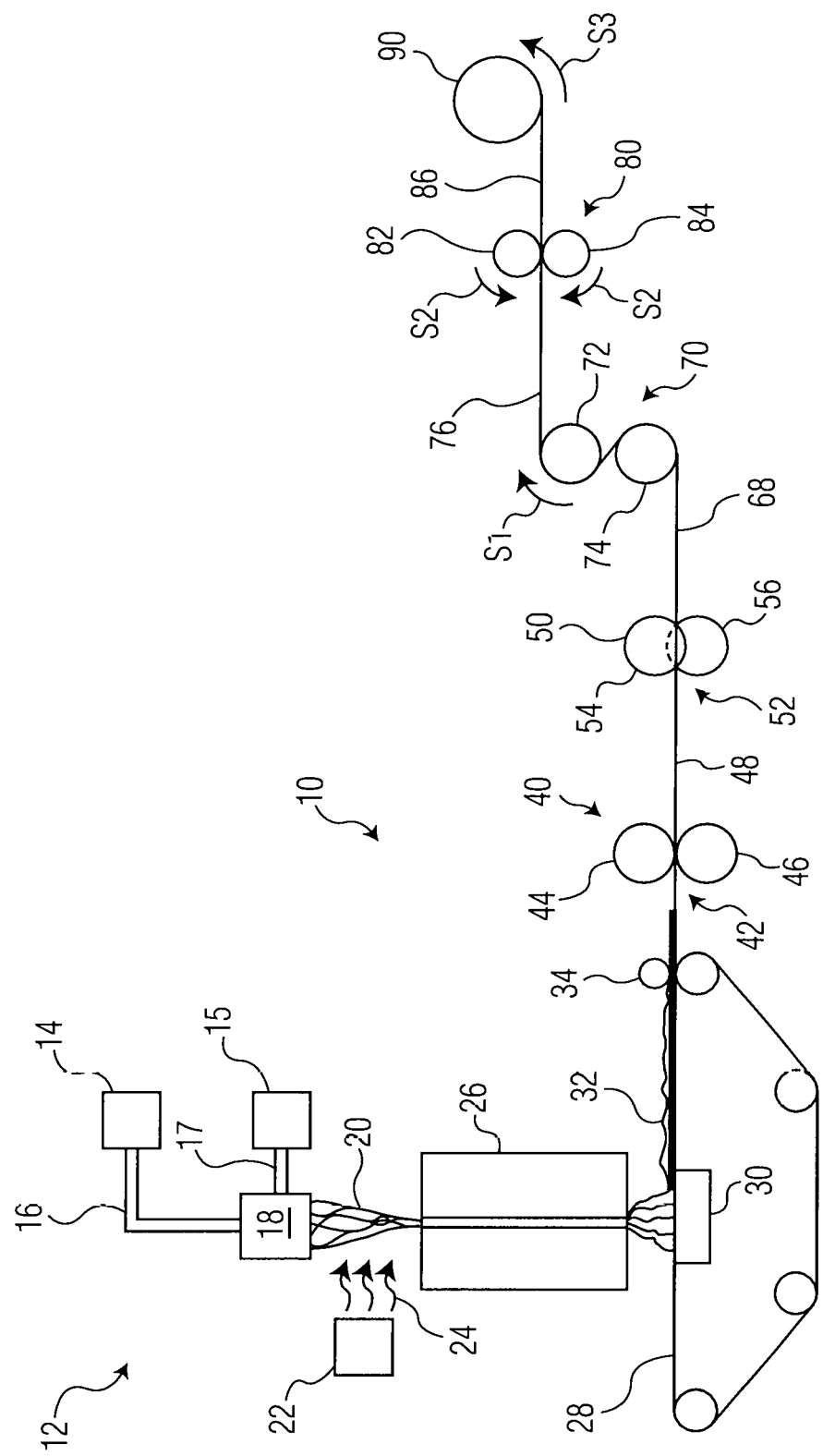
FIG. 1 is a schematic side-view of a process for making pattern bonded webs of the present invention

Throughout the specification and claims, discussion of the articles and/or individual components thereof is with the understanding set forth below.

As used herein, the term "comprising" or "including" or "having" are inclusive or open-ended and do not exclude additional unrecited elements, compositional components, or method steps. Accordingly, the terms "comprising" or "including" or "having" encompass the more restrictive terms "consisting essentially of" and "consisting of."

As used herein a "sequent pattern" means a pattern that includes a series of closely spaced bond points following one after the other and including patterns forming straight lines, curved lines, patterns including both straight and curved lines, branched or unbranched linear and curvilinear patterns, and so forth.

As used herein, the term "machine direction" or "MD" refers to the direction of travel of the forming surface onto which fibers are deposited during formation of a fibrous web; such direction also being the direction in which the fibers predominantly extend.

As used herein, the term "cross-machine direction" or "CD" refers to the direction which is essentially perpendicular to the machine direction defined above.

As used herein, the term "nonwoven web" means a structure or a web of material that has been formed without use of traditional fabric forming processes such as weaving or knitting, to produce a structure of individual fibers or threads that are entangled or intermeshed, but not in an identifiable, repeating manner. Non-woven webs can be formed by a variety of processes including, for example, meltblowing processes, spunbonding processes, staple fiber carding processes, and air laid and wet laid processes.

As used herein "spunbond" fibers and "spunbond" nonwoven webs comprise continuous fiber webs formed by extruding a molten thermoplastic material from a plurality of fine, usually circular, capillaries as molten threads into converging high velocity air streams which attenuate the filaments of molten thermoplastic material to reduce their diameter. The eductive drawing of the spunbond process also acts to impart a degree of crystallinity to the formed polymeric fibers which provides a web with relatively increased strength. By way of non-limiting example, spunbond fiber nonwoven webs and processes for making the same are disclosed in U.S. Pat. No. 4,340,563 to Appel et al, U.S. Pat. No. 5,382,400 to Pike et al.; U.S. Pat. No. 8,246,898 to Conrad et al., U.S. Pat. No. 8,333,918 to Lennon et al. and so forth.

As used herein "meltblown" fibers and "meltblown" nonwoven webs generally refer to those formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter. Thereafter, the meltblown fibers are carried by the high velocity gas stream and are deposited on a collecting surface to form a web of randomly dispersed meltblown fibers. By way of non-limiting example, meltblown fiber nonwoven webs and processes for making the same are disclosed in U.S. Pat. No. 3,849,241 to Butin, et al., U.S. Pat. No. 4,775,582 to Abba et al., U.S. Pat. No. 4,707,398 to Wisneski et al., U.S. Pat. No. 5,652,048 to Haynes et al, U.S. Pat. No. 6,972,104 to Haynes et al. and so forth.

As used herein "personal care articles" means any and all articles or products used for personal health or hygiene including diapers, adult incontinence garments, absorbent pants and garments, tampons, feminine pads and liners, bodily wipes (e.g. baby wipes, perineal wipes, hand wipes, etc.), bibs, changing pads, bandages, and components thereof.

As used herein "protection articles" means all articles intended to protect a user or equipment from contact with or exposure to external matter including, for example, face masks, protective gowns and aprons, gloves, caps, shoe covers, equipment covers, sterile wrap (e.g. for medical instruments), car covers, and so forth.

Method of Making the Nonwoven Fabrics

The aspects of the present invention may be employed in connection with a wide variety of nonwoven fabrics. Nonwoven webs suitable for use in the present invention include, but are not limited to, those made by spunbonding, meltblowing, hydroentangling processes, etc. In addition, multi-layer nonwoven laminates may also be used in connection with the present invention. Examples of suitable nonwoven fabrics and methods of making the same include, but are not limited to, those described in U.S. Pat. No. 5,382,400 Pike et al., U.S. Pat. No. 5,492,751 to Butt et al., U.S. Pat. No. 6,224,977 Kobylivker et al., U.S. Pat. No. 8,603,281 to Welch et al., WO99/32699 to Stokes et al. and WO16/080960 to Kupelian et al. The nonwoven web desirably comprises continuous or substantially continuous fibers such as, for example, those formed by spunbond fiber nonwoven web processes. Nonwoven matts or webs suitable for use in the process of the present invention can have a basis weight less than about 60 g/m$^2$. In certain embodiments, the nonwoven webs can have a basis weight less than about 45 g/m$^2$, 35 g/m$^2$, 30 g/m$^2$, 25 g/m$^2$, 20 g/m$^2$, or even 18 g/m$^2$ and further, in certain embodiments, can have a basis weight in excess of about 8 g/m$^2$, 10 g/m$^2$ or 12 g/m$^2$.

A wide variety of thermoplastic polymer compositions are believed suitable for use in connection with the present invention. By way of non-limiting example, suitable thermoplastic polymers include polyesters (e.g., polylactic acid, polyethylene terephthalate, etc.); polyolefins (e.g., polyethylene, polypropylene, polybutylene, etc.); polytetrafluoroethylene; polyvinyl acetates; polyvinyl chloride acetates; polyvinyl butyrals; acrylic resins (e.g., polyacrylate, polymethylacrylate, polymethylmethacrylate, etc.); polyamides (e.g., nylon); polyvinyl chlorides; polyvinylidene chlorides; polystyrenes polyvinyl alcohols; polyurethanes; and blends and combinations thereof. In one embodiment, for instance, the thermoplastic composition may comprise a polyolefin composition including greater than 50 weight percent polyolefin such as between about 51 to 99 weight percent, 60 to 98 weight percent, or even 80 to 98 weight percent of the thermoplastic composition. Suitable polyolefins include, for example, homopolymers, copolymers and terpolymers of ethylene (e.g., low density polyethylene, high density polyethylene, linear low density polyethylene, etc.), propylene (e.g., syndiotactic, atactic, isotactic, etc.), butylene and so forth. The polymer composition may comprise a homopolymer or homogeneous or non-homogeneous blends of two or more thermoplastic polymers. Further, as is known in the art one or more additives may added to the thermoplastic polymer composition including for example, adding one or more fillers, colorants (e.g. TiO2), antioxidants, softening agents, surfactants, slip agents and so forth. In particular, as is well known in the art, one or more slip agents, such as fatty acid amides, may be added to the polymeric composition for melt spinning.

The fibers used to form the nonwoven web may comprise monocomponent, multiconstituent and/or multicomponent fibers. Multicomponent fibers include polymer compositions that may be arranged in substantially constantly positioned distinct zones across the cross-section of the fibers and are generally formed from two or more polymer compositions (e.g., bicomponent fibers) extruded from separate extruders but spun together. The components may be arranged in any desired configuration, such as sheath-core, eccentric sheath-core, side-by-side, pie, island-in-the-sea or various other arrangements known in the art. Multiconstituent fibers refers to fibers which have been formed from at least two polymers extruded from the same extruder as a blend. In multiconstituent fibers the various polymers are usually not continuously positioned along the length of the fiber, instead usually forming fibrils or protofibrils which start and end at random. By way of example only, various methods for forming multicomponent and multiconstituent fibers are described in U.S. Pat. No. 4,795,668 to Krueger, et al., U.S. Pat. No. 5,108,820 to Kaneko, et al., U.S. Pat. No. 5,162,074 to Hills, U.S. Pat. No. 5,336,552 to Strack et al., U.S. Pat. No. 5,382,400 to Pike et al., US2001/0019929 DeLucia et al. and so forth.

In reference to FIG. 1, in one aspect the manufacturing process 10 can include a fiber forming apparatus 12, such as one for forming spunbond fiber nonwoven webs. The desired polymer composition is melted in an extruder 14 and directed through a conduit 16 to a spinneret 18. Optionally, such as when making multi-component or multi-constituent fibers, a second polymer is melted via second extruded 15 and simultaneously directed to the spinneret 18 via a second conduit 17. The one or more molten polymers are then extruded through the orifices (not shown) of the spinneret 18 to form fibers 20. The fibers are solidified or quenched via relatively cool air 24 provided by a blower 22. The quenched fibers 20 are then fed into a fiber drawing unit 26 which acts to further reduce the diameter of the fibers. The fibers then exit the bottom of the fiber drawing unit 26 and are deposited onto a forming wire 28 and form a relatively loose matt or web of fibers 32. Typically, a vacuum 30 is positioned beneath the forming wire 28 to help draw and place the fibers on to the forming wire 28. Optionally, the matt of fibers can be treated in order to impart some minimal degree of integrity required for additional handling. Such treatment may, for example, include consolidating the matt with a compaction roll 34. Optionally (not shown), the matt of fibers may be treated by the use of a high velocity through-air bonder, such as described in U.S. Pat. No. 5,707,468 to Arnold et al., the entire contents of which are incorporated herein by reference. Also, for certain nonwoven webs, it will be appreciated that nonwoven webs with sufficient integrity can optionally be manufactured separately and unwound from a supply roll (not shown).

After formation, the nonwoven matt is pattern bonded. The matt may be treated by one or more bonding techniques known in the art that impart localized compression and bonding corresponding to a desired pattern. In this regard, the matt can be point bonded by the application of localized pressure, heat, and/or ultrasonic energy. In certain aspects, the matt may be pattern bonded, as is known in the art, using a pair of bonding rolls, wherein at least one of the rolls has a pattern of protuberances or "pins" corresponding to the desired pattern of bond points to be imparted to the matt. The two cooperative rolls form a nip through which the matt is passed with the application of pressure and, optionally, heat. While suitable bond elements may be formed without the application of heat, use of heat together with pressure is generally preferred. The bonding can be conducted as is known in the art employing a nip formed by patterned roll and a smooth anvil roll ("pin-to-flat") or by two coordinated patterned rolls ("pin-to-pin"). With respect to the use of a smooth anvil roll, the roll may be a steel roll or alternatively may be coated with a resilient material. By way of example only, various pattern bonding methods are shown and described in U.S. Pat. No. 3,855,046 to Hansen et al., U.S. Pat. No. 4,333,979 to Sciaraffa et al., U.S. Pat. No. 4,374,888 to Bornslaeger, U.S. Pat. No. 5,110,403 to Ehlert, U.S. Pat. No. 6,165,298 to Samida et al. and so forth. As is known in the art, the pressures, temperatures, residence time, base sheet composition, basis weight, and other parameters will impact the selection of the desired degree of pressure and/or heat applied to the base sheet to form the bond points. Nevertheless, in many embodiments, it will be desirable to apply a contact pressure in the nip of between about of between about 3200 kg/cm$^2$ (about 45,000 PSI) and about 4600 kg/cm$^2$ (about 65000 PSI) or, in alternate embodiments, between about 3400 kg/cm$^2$ (about 48,000 PSI) and about 4200 kg/cm$^2$ (about 60,000 PSI). In addition, when the fibers comprise polypropylene fibers, one or more of the bonding rolls can have a temperature of between about 130° C. and about 155'C.

With respect to bonding the nonwoven web, it is important that the bonding seek to achieve strong bond points that are capable of acting as an anchor to the fibers during the various stretching steps. However, over bonding of the nonwoven web can result in a web that is generally stiffer as a result of over melting of fibers both in and around the bond sites. In this regard, over bonding can be associated with the formation of bond points that have been completely reduced to a homogeneous flat film, such that remnants of the fibers are no longer distinguishable, and/or that causes melting of fibers outside of the desired bond area. Further, under bonding of the nonwoven web will prevent the bond points from effectively acting as an anchor to the fibers during stretching and achieving the desired softening and bulking improvements. Further, both over and under bonding can lead to an increase in the incidence of tears or other visual defects. As may be seen in reference to FIGS. 6-9, at the bond points, the thermoplastic fibers are flatted and polymer is caused to soften and flow as a result of the localized application of heat and pressure. The bonding steps cause the bond points to have a substantially flat, melded surface. However, remnants of the original fibers can still be seen under microscopic analysis of the regions forming the bond points. Further, fibers outside of the bond points are not melded or bonded together as a result of the point bonding operation.

Figure 1A:
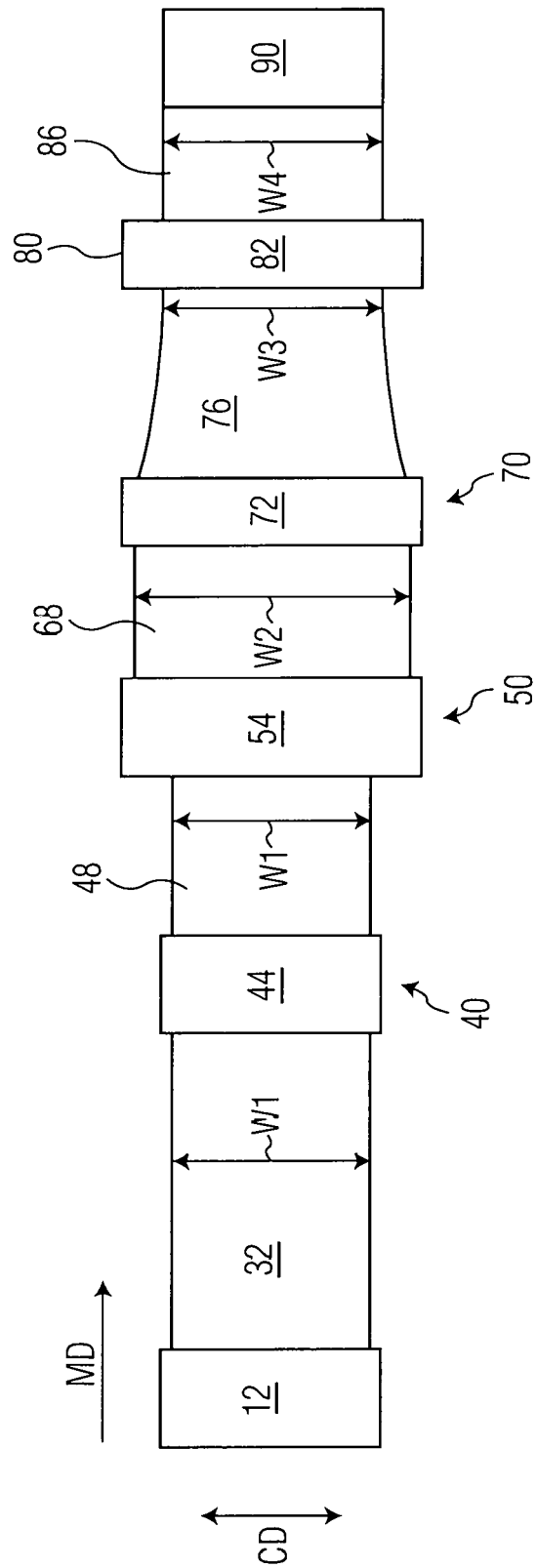
FIG. 1A is a schematic top-view of the process of FIG. 1.

Back in reference to the embodiment of FIGS. 1 and 1A, the matt 32 exiting the fiber forming apparatus 12 has an initial CD width (W1) and is directed to a pattern bonding assembly 40 including a pair of bonding rolls 44, 46. The bonding rolls 44, 46 form a nip 42 through which the matt 32 travels and while in the nip 42 a pattern of bond points is imparted thereto. Point bonded nonwoven fabric 48 exits the nip 42 of the bond roller assembly 40. Typically, the CD width (W1) of the nonwoven web will remain substantially unchanged as a result of the pattern bonding process. Details regarding suitable bond patterns are provided herein below.

In an alternate embodiment (not shown), it will be readily appreciated that the point bonded nonwoven web could be fed from a supply roll as opposed to being directly melt-spun and formed in-line as depicted in the embodiment in FIG. 1.

The pattern bonded nonwoven web is directed to an apparatus for stretching the pattern bonded nonwoven web in the CD, i.e. increasing the CD width of the fabric. Stretching of the nonwoven web in the CD may be carried out by any means known to those skilled in the art including for example tenter frame equipment or by intermeshing grooved roll systems. Examples of various CD stretching systems believed suitable for use with the present invention include, but are not limited to, those described in U.S. Pat. No. 4,116,892 to Schwarz, U.S. Pat. No. 4,223,059 Schwarz, U.S. Pat. No. 4,517,714 to Sneed et al., U.S. Pat. No. 5,770,531 to Sudduth et al., U.S. Pat. No. 6,368,444 Jameson et al., and U.S. Pat. No. 7,198,742 to Gerndt. In reference to embodiment shown in FIGS. 1 and 1A, the point bonded nonwoven web 48 is directed to a grooved roll assembly 50 comprising inter-meshing first and second grooved rolls 54, 56.

Figure 2:
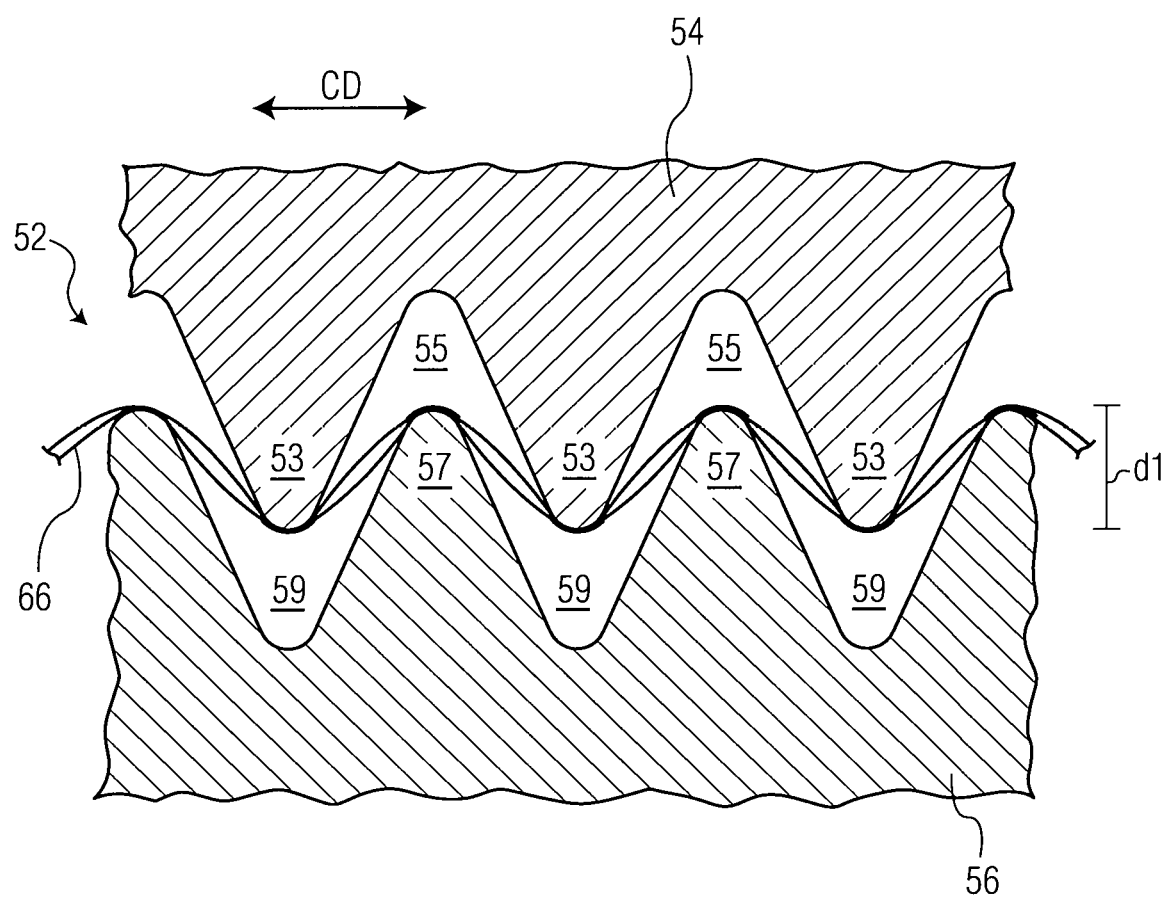
FIG. 2 is a portion of a nip of a grooved roll assembly suitable for use in connection with the present invention.

With respect to the use of an inter-meshing grooved roll assembly, the amount of CD stretch imparted to the nonwoven web is a function of the depth to which the grooved rolls are set; the deeper the grooved rolls mesh, the greater is the percent extension in the CD. FIG. 2 is a cross-sectional view of a section of a nip 52 formed by inter-meshing first and second grooved rolls 54, 56 of grooved roll assembly 50. The nip 52 presents a series of troughs or grooves 55, 59 and projections or ridges 53, 57. The grooved rolls 54, 56 are positioned relative to one another such that the grooves 55 of the first or upper grooved roll 54 correspond with and mesh with the ridges 57 on the opposed second or lower grooved roll 56. Similarly, the ridges 53 on the upper grooved roll 54 correspond and mesh with the grooves 59 of the opposed lower grooved roll 56. The opposed grooves and ridges engage or mesh with one another to a selected depth (d1). In certain embodiments, the ridges and grooves will run concentrically around the entirety of the rolls 54, 56. In this regard, the grooves 53, 57 generally extend perpendicular to the direction of stretch of the material. As the point bonded nonwoven web 66 is pulled within and through the nip 52, the engagement between corresponding ridges and grooves of the opposed rolls cause the nonwoven web 66 to be stretched in the widthwise or cross-machine direction particularly in the unengaged areas extending between the tops of the ridges 53, 57. The grooves or troughs of such grooved rolls may be machined into a roll, may be a series of elements such as discs, or may be any other means that provides the functional structure shown. It will be apparent that the number of engaging rolls and the engagement depth of the respective rolls may be varied, and the rolls may be partially or fully grooved to provide zoned or full stretching along the roll length as desired. Also, the addition of heat in the grooved rolls or during cross-machine direction stretching can in certain embodiments enhance widthwise extension.

In certain embodiments the size and spacing of the ridges and grooves contained on a single roll may vary. For example, a single roll may have between about 0.25 grooves per cm (i.e. about 1 every 4 cm) and about 5 grooves per cm, and in some embodiments from about 0.5 grooves per cm and 4 grooves per cm, and in still other embodiments between about 1 and about 3 grooves per cm. The grooves may also have a certain depth and/or the ridges a certain height such as, for example, being between about 0.15 cm to about 4 cm or, in other embodiments, between about 0.2 cm and about 2 cm. In addition, the peak-to-peak distance of the ridges between the grooves can also vary such as in certain embodiments being between about 4 cm to about 0.2 cm, and in other embodiments being between about 2 cm to about 0.25 cm, and in still further embodiments being between about 1 and about 0.34 cm. Further, by arranging the gap distance between the rolls, the nonwoven material can be engaged to varying degrees corresponding in part to the engagement depth (d1) which can in certain embodiments range from about 10-90%, from about 30-85% or even between about 50-80% of the depth of the ridges and/or grooves. In certain embodiments, the engagement depth (d1) may be between about 1.2 mm and about 3.5 mm, between 1.5 mm and 3 mm or even between about 1.8 mm and about 2.8 mm. Further, in order to limit the compression of the nonwoven fabric, typically the shape of the intermeshing grooves and ridges and the corresponding gaps provided will be selected in relation to the thickness of the nonwoven material so as to reduce or eliminate the extent of compression caused by the sides of the grooves.

As indicated above the size, shape and number of grooves may be varied in order to achieve the desired CD stretch. In this regard, the total CD stretch imparted to the material is at least 1% and in certain embodiments can be between about 1 and about 12%, between about 2% and about 10% or even between about 2 and about 8%. As best seen in reference to FIG. 1A, as a result of the CD stretching provided by the grooved roll assembly 50, the width ($W_2$) of the nonwoven fabric 68 exiting the nip of the grooved roll assembly 50 is larger than the width ($W_1$) of the point bonded nonwoven web 48 entering the grooved roll assembly 50. Further, it is noted that the CD stretching also acts to decrease the overall basis weight of the nonwoven web. Further, the grooved rolls can impart to the nonwoven web a grooved three-dimensional shape generally corresponding to the ridges and grooves of the grooved rolls.

The CD oriented nonwoven fabric may then be stretched in the MD so as to neck the fabric. As used herein, the terms "necking" or "neck stretching" interchangeably refer to a method of elongating a nonwoven fabric, generally in the machine direction, to reduce its CD width in a controlled manner to a desired amount. The controlled stretching may take place under cool, room temperature or higher temperatures and is limited to an increase in the overall length in the MD dimension in the direction being stretched up to the elongation required to break the fabric. The neck stretching may be achieved by various means known in the art such as those described in, but not limited to, U.S. Pat. No. 4,443, 513 to Meitner et al., U.S. Pat. No. 4,981,747 to Morman and U.S. Pat. No. 5,244,482 to Hassenboehler Jr. et al.

In accordance with one embodiment of this invention, necking of the nonwoven web is achieved by applying a machine direction tensioning force thereto. In this regard, the CD stretched nonwoven material 68 can be directed to an S-wrap roller assembly 70 formed by stacked rolls 72, 74 that operate at a first circumferential speed (S1). The nonwoven web exits the S-wrap roll assembly 70 and is directed to a drive roll assembly 80 comprising a nip formed by a pair of drive rollers 82, 84. The drive rollers 82, 84 operate at a second circumferential speed (S2) that is higher than the first circumferential speed (S1) of the S-wrap assembly 70. The increased speed imparts an MD stretching force on and necks nonwoven web 76. The necking results in a nonwoven web 76 having a reduced CD width (W3) relative to the CD width (W2) of the CD stretched nonwoven web 68. In certain embodiments, the speed differential as between the upstream and downstream roll assemblies is between about 0.2 and 3.5%, between about 0.4 and about 3% or in other embodiments between about 0.5 and about 2.5%. For example, in reference to the system depicted in FIG. 1, a speed differential of 1% means that the circumferential speed of the s-roll assembly 70 is 1% slower than the circumferential speed of the drive roll assembly 80. Similarly, at a 1% speed differential, the web is travelling 1% faster within the drive roll assembly 80 relative to the speed within the s-wrap assembly 70. In a further aspect, the CD oriented nonwoven web 68 is pulled with sufficient force in the MD so as to cause the CD width (W2) to decrease at least 0.5%. For example, in certain embodiments, the CD width (W2) of the CD oriented material 68 can be necked down or decreased in the CD between about 0.5 and about 3.5%, between about 0.7 and about 3% or even between about 0.7 and about 2.5%. In other words, necking the CD oriented material 68 results in a necked material 76 having a reduced CD width; i.e. in reference to FIG. 1A the CD width W3 is between about 0.5% and 3.5% less than CD width W2. Necking the bonded nonwoven fabrics having the bond patterns described herein, results in nonwoven webs having significantly improved softness and bulk but with little loss of tensile strength and/or significantly diminished formation of visual aberrations or defects and in particular visually discernable tears.

After necking, the treated nonwoven web can be slit and directly fed into converting operations such as inclusion within one or more components of a personal care article. Alternatively, as shown in the embodiment depicted in FIGS. 1 and 1A, the treated nonwoven web 86 can be wound onto a wind-up roll 90 operating at a third circumferential speed (S3). The speed (S3) of the wind-up roll 90 can be the same or substantially the same as the speed (S2) of the drive roll assembly 80. As still a further alternative, the speed (S3) of the wind-up roll 90 may be slightly slower than that of the drive roller assembly 80 thereby allowing the necked nonwoven web 76 to relax, and upon relaxation the web 86 may recover to some extent towards its pre-necked dimensions and resulting in a final CD width (W4) that is slightly larger than the CD width (W3) of the necked nonwoven 76.

The treated nonwoven fabrics 86 desirable have a basis weight less than less than about 60 g/m$^2$. In certain embodiments, the nonwoven webs can have a basis weight less than about 45 g/m$^2$, 35 g/m$^2$, 30 g/m$^2$, 25 g/m$^2$, 20 g/m$^2$, or even 18 g/m$^2$ and further, in certain embodiments, can have a basis weight in excess of about 8 g/m$^2$, 10 g/m$^2$ or 12 g/m$^2$. Further, the treated nonwoven fabric also has a tensile strength of at least about 50 g-f including for example having a tensile strength greater about 100 g-f, 150 g-f, 200 g-f, 250 g-f or even 300 g-f and, in certain embodiments, a tensile strength less than about 5000 g-f, 3000 g-f, 2500 g-f, 2000 g-f or even 1500 g-f.

The process of the present invention can provide a soft, bulky and strong nonwoven web. In certain aspects, the nonwoven web can have alternating first and second sections extending in the MD, such first and second sections generally corresponding with the location of the grooves and ridges of the inter-meshing grooved rollers. In this regard, in certain embodiments, a nonwoven web is provided having distinct first and second segments that differ topographically and wherein the first sections are on average at least 350 micrometers, 400 micrometers or even 425 micrometers higher than second sections (when the nonwoven web is laid on a flat surface). Further, the frequency of the sections will generally correspond with the ridges and grooves used to stretch the fabric, and thus the first sections can have a frequency of about 0.25 and about 6 per cm or between about 0.5 and about 5 per cm. Further, in certain embodiments the first section can have greater bulk than the second section, have a higher average thickness, and/or have a higher average basis weight than the second sections. The bulk or thickness of the nonwoven may be determined visually.

Those skilled in the art will readily appreciate that, while not shown, various additional potential processing and/or finishing steps known in the art may be conducted upon the nonwoven materials including, but not limited to, slitting, printing, laminating, electret treating, applying topical treatments or chemistries, and so forth.

Bond Pattern

As noted above, a particular bond pattern is utilized in order to obtain increased fabric bulk and softness and yet which does not suffer from regular tearing that results in either a loss of sheet strength or formation of superficial defects noticeable to the naked eye. In this regard, tears visible to a consumer, even when not substantial enough to cause a significant degradation in properties, can erode the user's confidence in the ability of the sheet and related component to perform its intended function. For example, in relation to a nonwoven/film laminate used as a baffle, the sight of even small tears may raise concerns over leakage. In order to achieve the desired improved properties related to softness, bulk and visual appearance, a bond pattern is selected having a combination of various parameters as discussed below.

In one aspect, the bond points forming the pattern will comprise small, discrete individual bond points. In certain embodiments, the bond points will have a bond area less than about 5 mm$^2$ and, in certain embodiments, can have a bond area between about 0.5 mm$^2$ and about 5 mm$^2$ or even between about 0.8 mm$^2$ and about 3 mm$^2$. In a further aspect and in reference to FIG. 4, the individual bond points can have maximum dimension (d2), e.g. a diameter extending in its greatest dimension, less than about 1.25 mm, 1.15 mm, 1.0 mm or even less than about 0.9 mm. In a further aspect, the discrete, individual bond points forming the pattern will have a minimum dimension of not less than 0.38 mm or, in other embodiments, not less than about 0.5 mm. The shape of the individual bond points can vary such as, for example, being round, elliptical, square, triangular and so forth. However, shapes without sharp corners or segments are generally preferred. In addition, the individual bond points can have an aspect ratio of less than about 3:1, 2.5:1, 2:1 or even 1.5:1; where the length is the greatest dimension and the width is the dimension perpendicular thereto. Circular shaped bond points are generally preferred. For example, and in reference to the particular embodiment depicted in FIGS. 3 and 4, bond pattern 100 is formed by circular shaped individual bond points 110.

In addition, suitable patterns will arrange the individual bond points in a sequent pattern or grouping so as to create individual macro-design elements. As one example, and still in reference to FIGS. 3 and 4, the individual bond points 110 are grouped in a generally linear or curvilinear manner to form macro-design elements 112. The individual macro-elements may be the same or differ from one another. For example, pattern 100 includes a first macro-element 112A and a second macro-element 112B having a different shapes from one another. The closely spaced bond points forming the macro-design elements may be positioned proximate one another being spaced apart an edge-to-edge distance of not more than 0.8 mm such as, for example, being between about 0.03 mm and 0.8 mm, between about 0.04 mm and 0.7 mm or even between about 0.05 mm and 0.6 mm. As best seen in reference to FIG. 4, the distance between adjacent individual bond points 110 is determined by drawing a line between the closest edges of the two bond points, an example of such a line and distance being shown as d3. The individual bond points forming the macro-elements are provided in a sequent pattern such as, for example, those forming linear or curvilinear elements as well as branched or unbranched versions of the same. Examples include, but are not limited to, elements having a zig-zag, sinusoidal, crescent, S, 3, or J shapes as well as shapes having multiple irregular curves. The sequent pattern forming the macro-elements will extend substantially in the machine direction, i.e. between +/−25 of MD, and in certain embodiments the macro-elements may be oriented and extend +/−20, +/−15 or +/−10 of the MD. In this regard, by way of example and as shown in FIG. 4, the direction or angle of the macro-element is determined by drawing a straight line from the outer distal MD edges of the of the uppermost and lowermost bond points 110U, 110L forming the macro-element 112 and then determining the angle θ relative to the MD line.

The bond pattern comprises numerous macro-elements each of which extends only a limited length in the MD. In this regard, the macro-elements desirably have an MD length of less than about 25 mm, 20 mm, 15 mm or even less than about 12 mm and, in certain embodiments, an MD length greater than about 4 mm, 5 mm, 6 mm or even 7 mm. The MD length, designated d4 in FIG. 4, is measured as between the outer most MD edges of the uppermost and lowermost bond points 110U, 110L by drawing a tangent line extending in the CD and drawing a line in the MD as between the 2 tangent lines. In a further aspect, the overall density of the macro-elements can be between about 1 and about 5 per cm$^2$ such as for example being between about 1.5 and about 4 per cm$^2$, or even being between about 1.5 and about 3.5 per cm$^2$.

In still a further aspect, in certain embodiments the macro-elements will have a CD width of at least 1 mm such as for example having an CD width of between about 1 and about 7 mm, or between about 1.5 and about 5 mm or even between about 1.5 mm and about 4 mm. The CD width is measured by drawing a tangent line extending in the MD from the outer edges of the individual bond points positioned furthest in the opposed CD directions, e.g. the bond points furthest to the left and furthest to the right in reference to FIG. 4. Still in reference to FIG. 4, MD tangent lines are drawn to the distal most CD bond points, 110C and 110D, and the CD distance between the two tangent lines is the macro-element width, designated d5.

In a further aspect, the closest bond points of adjacent macro-elements are spaced apart from one another (d6) to a greater degree than the spacing of bond points forming the macro-elements. In this regard, the closest bond points of adjacent macro-elements are spaced apart from one another a minimum distance of not less than 0.9 mm. In a further aspect, the closest bond points of adjacent macro-elements can be spaced apart from one another a distance of between about 0.9 to about 4 mm, between about 0.9 to about 3 mm, between about 0.9 to about 2.5 mm, between about 1 mm to about 3.5 mm, between about 1 mm to about 3 mm, between about 1 mm to about 2.5 mm or between about 1 mm and about 2.25 mm. For example, the macro-element to macro-element spacing d6, is calculated as between the proximate outer edge of the closest bond points of adjacent macro-elements. For example, in reference to FIG. 4, macro-element to macro-element spacing (d6) is calculated as between the lower most bond element 110L of the upper macro-design element 112U and of the proximate outer edge of the upper most bond element 110U of the closest lower design element 112L.

In a further aspect, in certain embodiments the individual macro-elements may have an aspect ratio, MD length:CD width, of at least 2.5:1 and desirably at least 3:1. By way of example, in certain embodiments the macro-elements hay have an aspect ratio of between about 25:1 and 2.5:1, 15:1 and 3:1, 12:1 and 3:1, 10:1 and 3:1 or even between 6:1 and 3:1.

Figure 3:
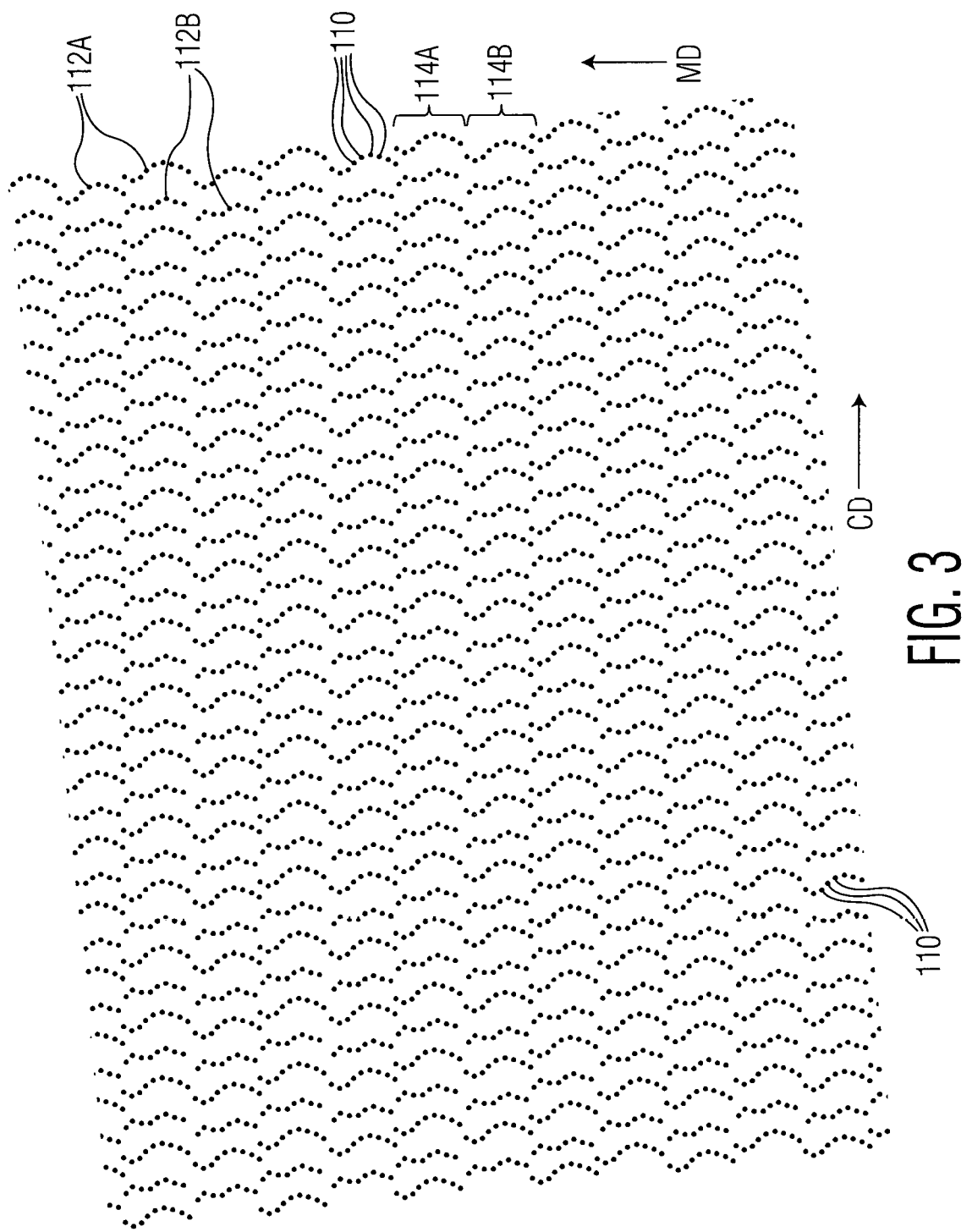
FIGS. 3 and 4 depict a bond pattern suitable for use in connection with the present invention.
Figure 4:
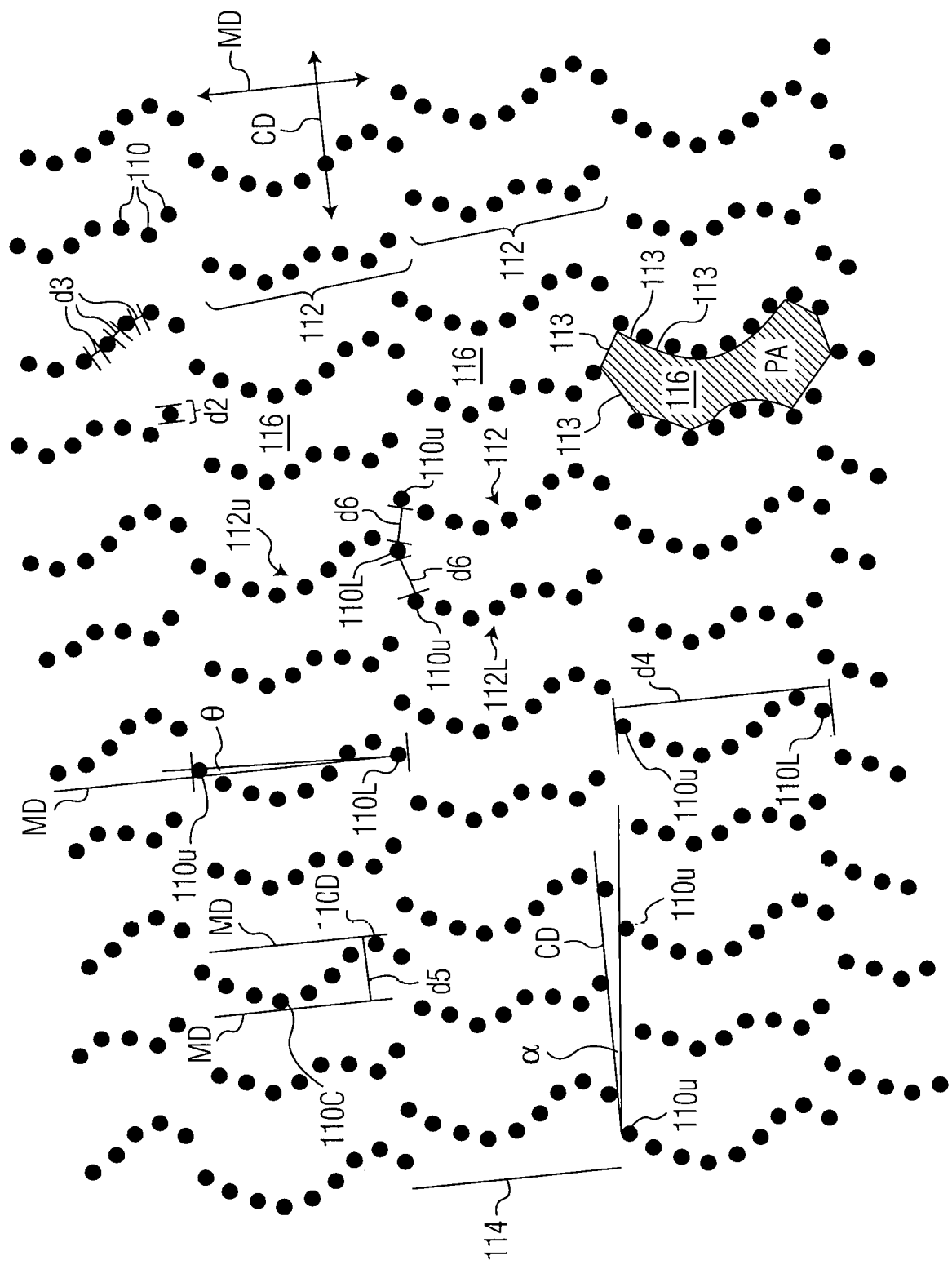

The bond pattern may comprise rows of the macro-elements, and as seen in reference to FIG. 3, the individual rows 114A, 114B can extend substantially in the CD. In certain embodiments the rows extend at angle slightly askew to the CD such as extending +/−15 degrees, +/−10 degrees or even +/−5 degrees relative to the CD. The row angle can be calculated relative to the CD by drawing a line extending along the outer edges of the uppermost bond points of the macro-elements forming the row. By way of example and in reference to FIG. 4, uppermost bond points 110U of macro-elements 112 within row 114 is drawn and the row angle (α) is measured relative to the CD line. In addition, the individual macro-elements within a row are spaced apart from one another so as to form an unbonded pocket 116 there between.

The spacing and row angles are selected such that a line extending in the CD will intersect at least one bond point. In other words, the macro-elements of adjacent rows are positioned so as to ensure there is no unbonded lane extending significantly in the CD. Further, rows of macro-elements can be staggered or off-set relative to on another such that the macro-elements of an upper row do not fully align or overlap an upper and/or lower macro-element.

As mentioned above, the spaced macro-elements form regions or pockets substantially free of bond points and the pockets will be sufficiently large so as to enhance softness and/or bulk. In this regard, the pockets 116 lie adjacent the macro-elements 112 and may present an area of at least 20 mm$^2$, 22 mm$^2$, or 25 mm$^2$ and in further aspects may present an area less than about 50 mm$^2$, 45 mm$^2$, or 40 mm$^2$. The pocket area, or PA, as between adjacent macro-elements 112 is determined by drawing lines 113 between the pocket facing edges of the individual bond points 110 in each of opposed macro-elements elements 112A, 112B thereby forming the lateral boundaries of the pockets. To define the upper and lower boundary of the pocket, lines 113 are drawn from the pocket facing edge of the upper most bond points 110U (or lower most bond points 110L as maybe applicable) of the macro-elements immediately overlying or underlying the pocket.

In addition, the spacing, CD width and macro-element angle can be selected such that no significant unbonded lane extends in the MD. In other words, the staggered or off-set macro-elements of adjacent rows are positioned so as to ensure there is no significant unbonded lane that extends through the pattern in the MD. In certain embodiments, an MD extending lane having a CD thickness of 1.5 mm will intersect at least one bond point in the pattern. In certain other embodiments, an MD extending lane having a CD thickness of 1 mm will intersect at least one bond point in the pattern. In still further embodiments, an MD extending lane having a CD thickness of 0.5 mm will intersect at least one bond point in the pattern. Further, it is important that the pockets not be fully occluded or surrounded by bond points. In this regard, unbonded sections corresponding to the macro-element to macro-element spacing (d6) will be adjacent multiple sections of the pocket's perimeter; for example, having 2, 3 or 4 of such unbonded sections adjacent the perimeter of the pocket.

In a further aspect, the bonded nonwoven fabric can have an overall bond area of less than about 20% and, in certain embodiments, have a bond area of between about 5 and about 18% or even between about 7 and about 15%.

Figure 9:
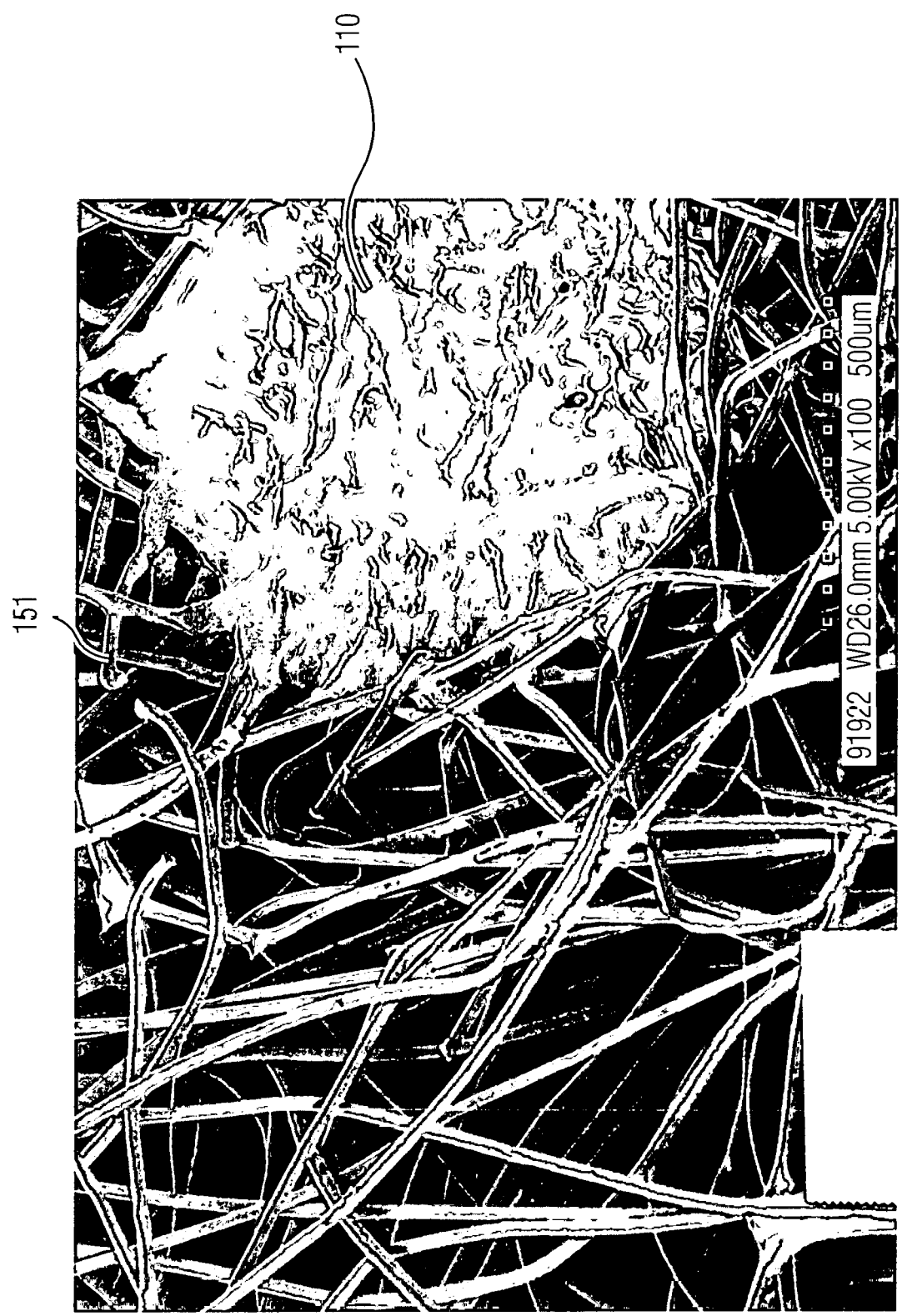
FIG. 9 is an SEM photomicrograph of a pattern bonded nonwoven web of the present invention after having undergone CD and MD mechanical stretching operations.

As noted previously, the pattern bonded nonwoven webs of the present invention are better suited to withstanding the CD and/or MD stretching operations associated with mechanical softening. In this regard, mechanically softened nonwoven webs can have a very low incidence of bond point tears or ruptures. In this regard, the pattern bonded webs of the present invention, after having undergone CD and/or MD softening treatments, can have ruptures in less than 2% of the bond points, less than 1% of the bond points, less than 0.5% of the bond points or even less than 0.1% of the bond points. While it is common for bond points to have holes therein when formed, resulting from areas lacking fibers and polymer, holes generated upon formation of the bond point are generally rounded and are bordered by flattened fibers or filmed-segments forming part of the bond point. However, ruptured or torn bond points present a jagged unconnected segment extending through and out of plane with the bond point and includes broken fibers and separated filmed-over segments from within the boundaries of the bond point. The formation of these ruptures is greatly reduced and/or avoided by the present process and bond pattern through the formation of numerous independent anchor points which hold fibers sufficiently in place to achieve the stretching and bulking benefits sought to be obtained through the stretching operations. Further, without being bound by a particular theory, it is believed that the pattern better distributes stress across the web and reduces stress localized at or within the bond points. In this regard, the stretching operations when performed on bonded nonwoven webs of the present invention act to distribute the stress more evenly and, while fiber breaks occur with these operations, they are better distributed around the bond points (such as seen in FIG. 9) and result in a substantial decrease in the number of bond point ruptures.

Use of the Nonwoven Web

The nonwoven webs of the present invention can be utilized in any one of numerous different end use applications. The nonwoven webs can be used alone or together with other layers or materials. With respect to multilayer structures, pattern bonded nonwoven webs of the present invention may be used as a layer in a multi-layer laminate such as comprising one or more layers within the following laminar materials: spunbond/meltblown; spunbond/meltblown/spunbond; spunbond/meltblown/meltblown/spunbond; spunbond/film; spunbond/film/spunbond; spunbond/meltblown/film; spunbond/meltblown/film/spunbond; spunbond/film/meltblown; spunbond/spunbond; spunbond/bonded-carded web; meltblown/bonded-carded web; etc. Exemplary laminate materials and end uses for the pattern bonded nonwoven webs include, but are not limited to, those described in U.S. Pat. No. 5,843,057 McCormack, U.S. Pat. No. 5,492,751 to Butt et al., U.S. Pat. No. 8,603,281 to Welch et al., U.S. Pat. No. 7,803,244 Siqueira et al., U.S. Pat. No. 6,115,839 to Covington et al., U.S. Pat. No. 6,811,638 to Close et al., WO98/53896 to Reader, U.S. Pat. No. 8,914,936 Jemsby et al., etc.

Figure 5:
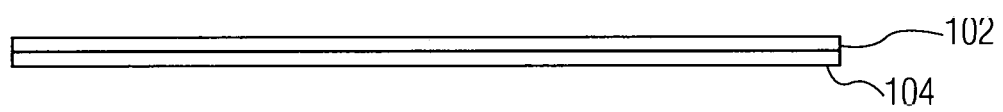
FIG. 5 is a side view of a multi-layer laminate containing a pattern bonded nonwoven web of the present invention.

As one example and in reference to FIG. 5, a multi-layer laminate 100 is provided comprising a pattern bonded spunbond nonwoven web 102, formed in accordance with the present invention, that is attached to a film 104. Various techniques may be utilized to bond the pattern bonded nonwoven web together with other layers including adhesive bonding, such as through gravure, slot or spray adhesive systems, thermal bonding, ultrasonic bonding and so forth.

In one aspect, the nonwoven webs may be used as a component of a personal care article either alone or together with other layers or materials. In this regard, the pattern bonded nonwoven webs are well suited to serving as a layer intended to come into contact with the skin. For example, the pattern bonded nonwoven web may comprise part of the liquid intake structure or liner. In a further aspect, the pattern bonded nonwoven webs may comprise an outer layer of a breathable baffle layer such as is commonly provided by a film/spunbond laminate. In still further aspects, the pattern bonded nonwoven webs may comprise the outer facing of an elastic component. In this regard, elastic materials, while desirable for their ability to enhance the fit of an article, often have a tacky or otherwise undesirable feel to the touch. Thus, the pattern bonded nonwoven webs are well suited for use as an outer facing in an elastic laminate.

In addition, the nonwoven webs may also be employed as a component of a protection article. In this regard, the pattern bonded nonwoven webs may comprise a facing layer for elastic materials such as may be employed in cuffs or other elastic panels within a garment. Still further, the pattern bonded nonwoven webs may be employed as a facing layer for a barrier laminate in which the barrier layer is often provided by a film or fine fiber meltblown web.

EXAMPLES

Example 1

Figure 6:
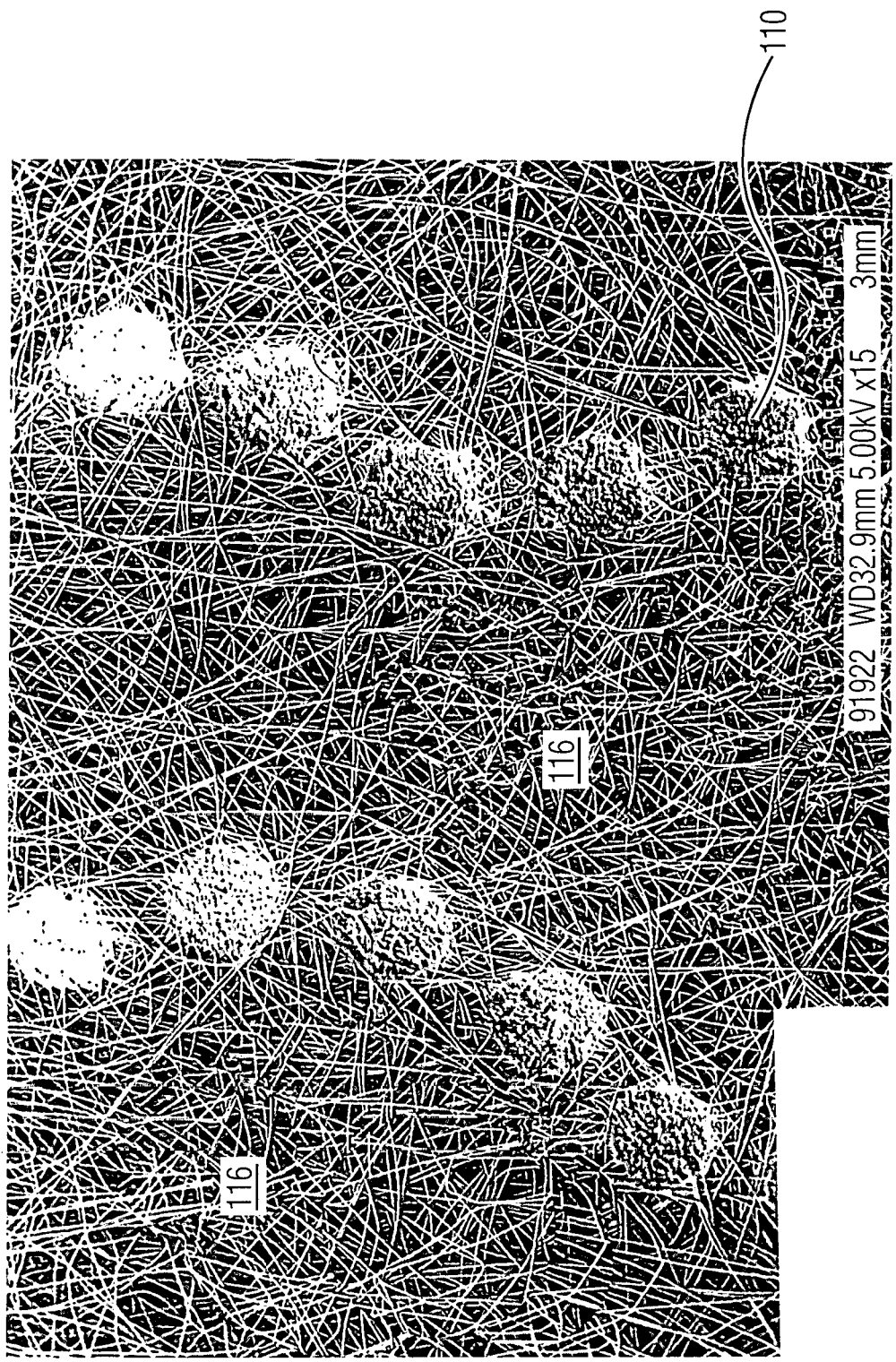
FIG. 6 is an SEM photomicrograph of a pattern bonded nonwoven web prior to undergoing mechanical stretching operations.

A propylene homopolymer spunbond fiber nonwoven web having a basis weight of 22 g/M$^2$ was pattern bonded with the pattern as shown in FIG. 3. An SEM photomicrograph of the resulting individual bond points 110 and unbonded pockets 116 is shown in FIG. 6. The pattern bonded nonwoven web was then subjected to a CD stretching process utilizing a pair of inter-meshing grooved rolls; the pattern bonded nonwoven web was stretched in the CD such that the overall width increased approximately 2%. An SEM photomicrograph of the CD stretched nonwoven web is shown in FIG. 7.

Figure 7:
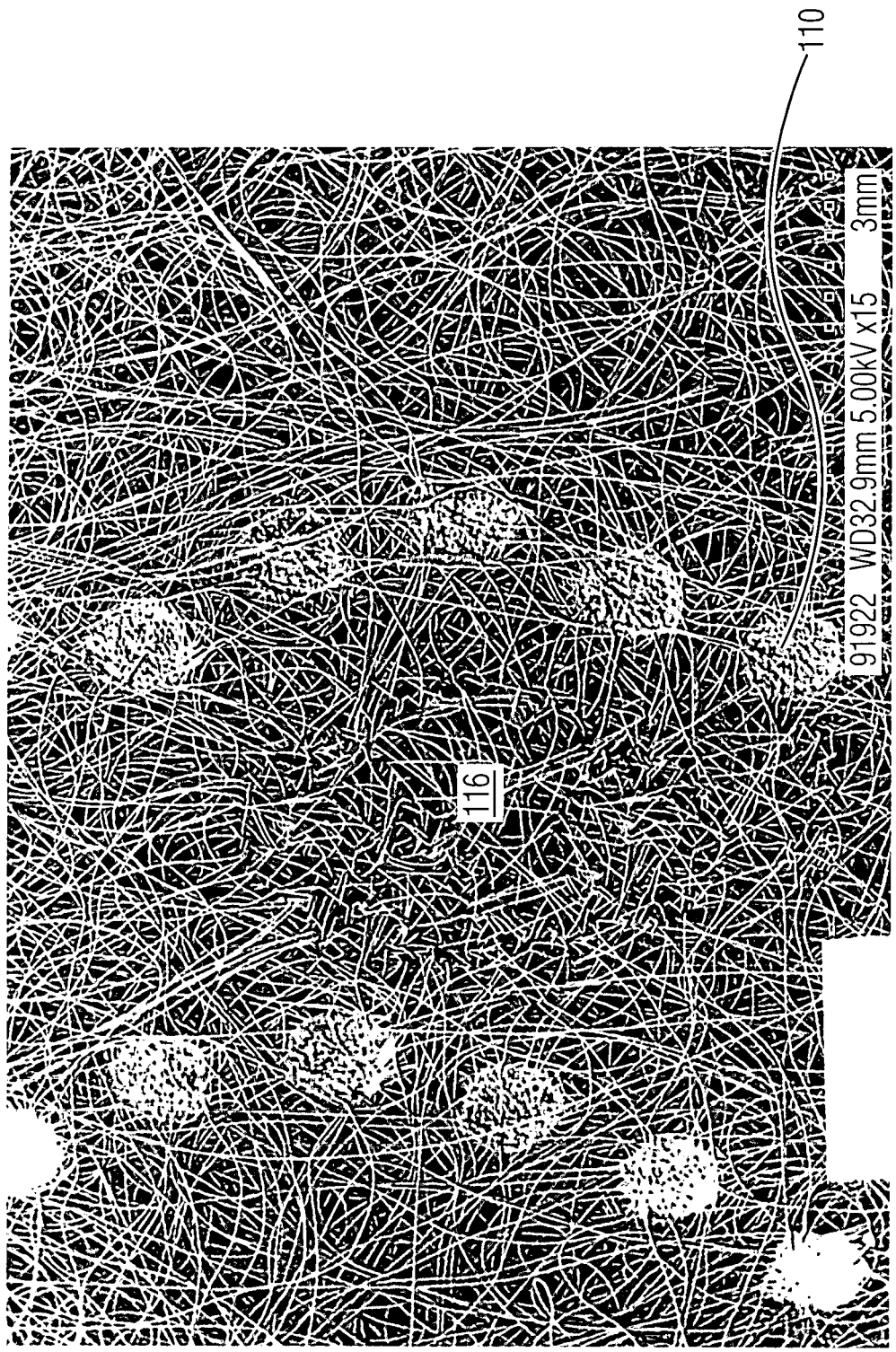
FIG. 7 is an SEM photomicrograph of a pattern bonded nonwoven web of the present invention after having undergone CD mechanical stretching operations.
Figure 8:
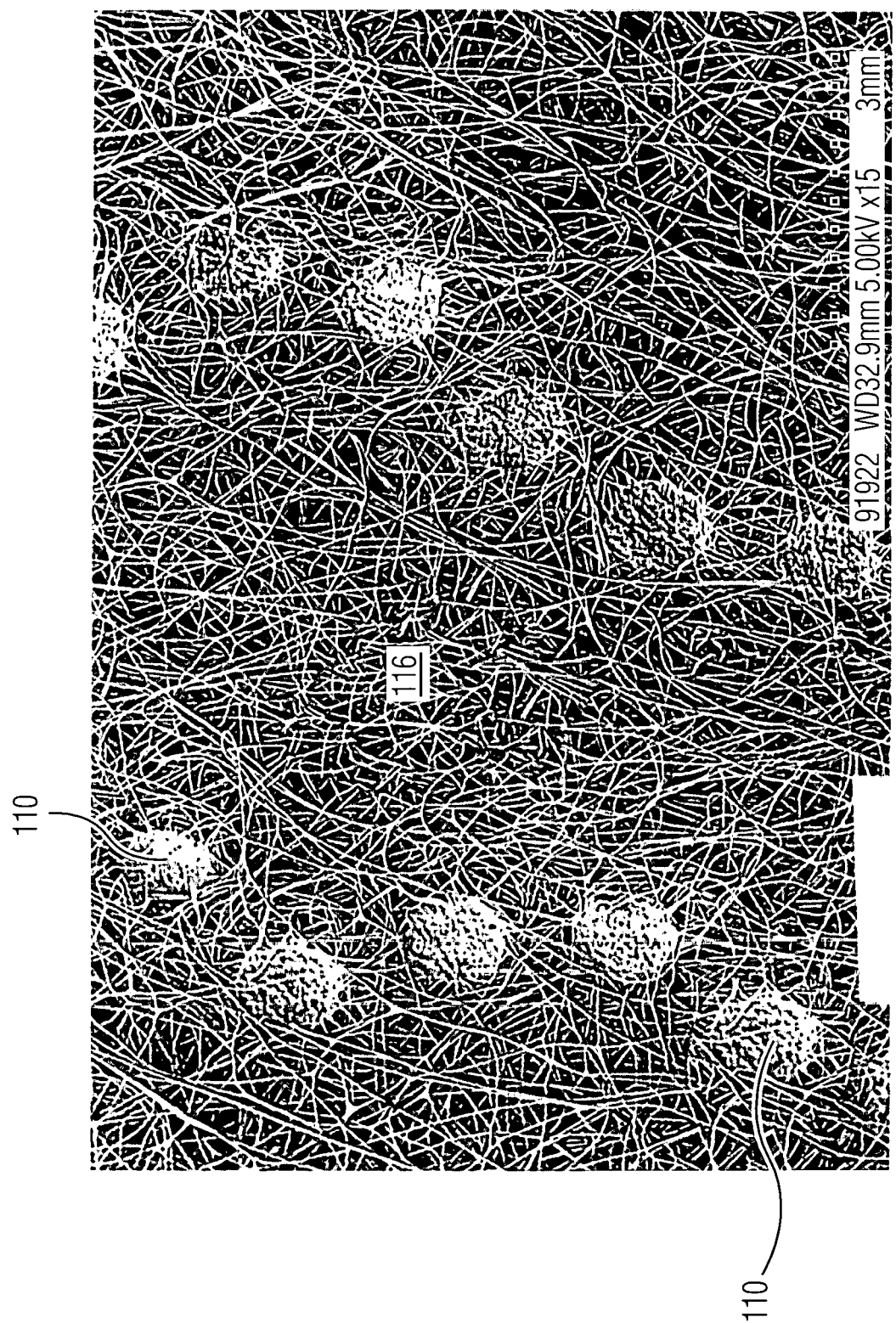
FIG. 8 is an SEM photomicrograph of a pattern bonded nonwoven web of the present invention after having undergone CD and MD mechanical stretching operations.

As may be seen upon the comparison of FIGS. 6 and 7, the individual bond points 110 remain intact and without rupture. The CD stretched nonwoven was then neck stretched by the application of a machine direction force thereby reducing the overall width by approximately 1.5%. An SEM photomicrograph of the MD and CD stretched nonwoven web is shown in FIG. 8 and as seen therein the bond points 110 still remain intact.

Comparative Example 2

Figure 10:
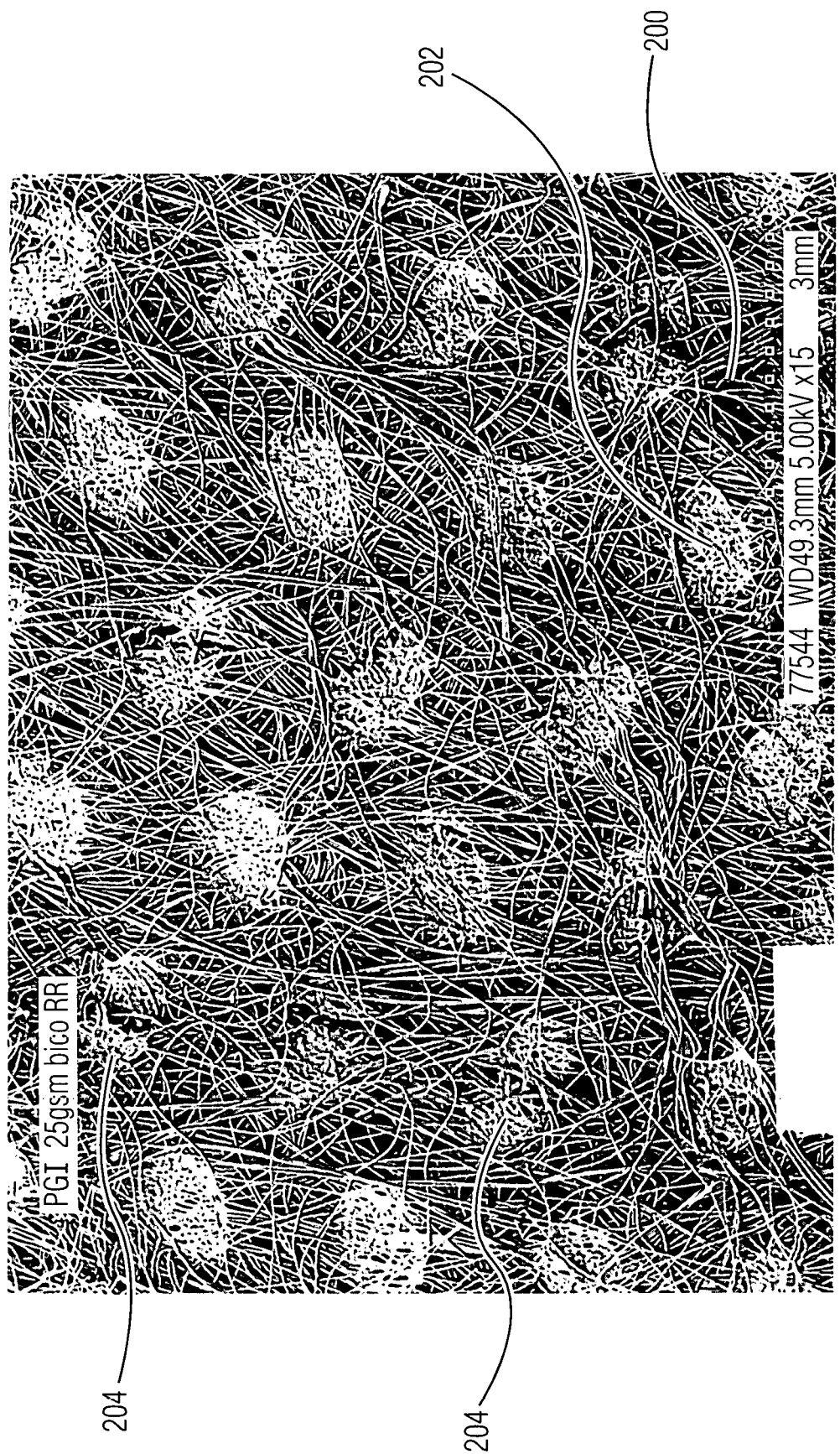
FIGS. 10 and 10A are SEM photomicrographs of a nonwoven web bonded with a prior art bond pattern that has undergone CD mechanical stretching operations.
Figure 10A:

A sheath/core PE/PP spunbond fiber nonwoven web having a basis weight of 25 g/M$^2$ was pattern bonded with a pattern having uniformly spaced generally oval shaped bond points. The pattern bonded nonwoven web was then subjected to a CD stretching process utilizing a pair of inter-meshing grooved rolls; the pattern bonded nonwoven web was stretched approximately 2% in the CD. An SEM photomicrograph of the CD stretched nonwoven web 200 is shown in FIGS. 10 and 10A and as shown therein a plurality of the individual bond points 202 have tears and/or ruptures 204.

Comparative Example 3

Figure 11:
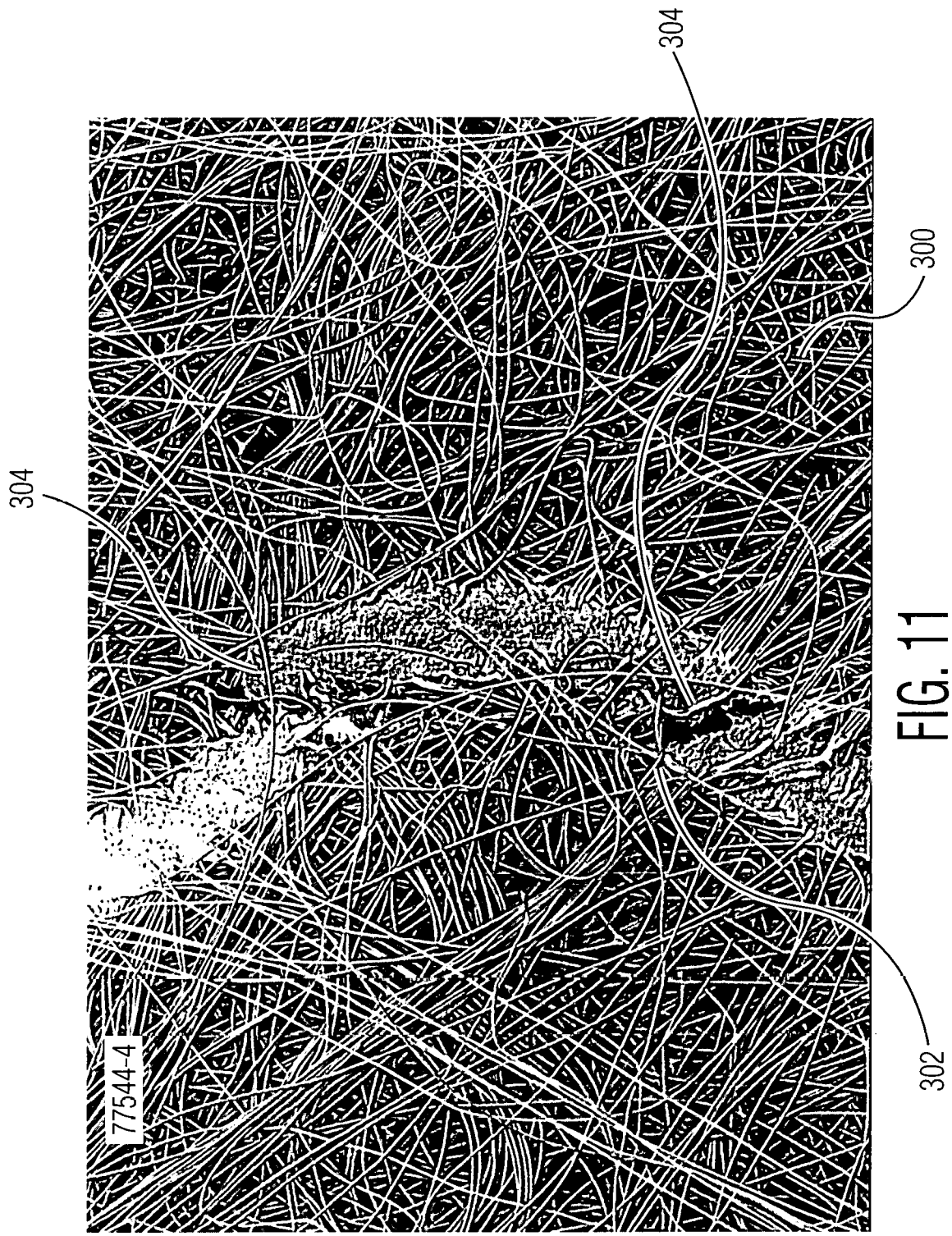
FIG. 11 is an SEM photomicrograph of a nonwoven web bonded with a prior art bond pattern that has undergone CD mechanical stretching operations.

A homopolymer polypropylene spunbond fiber nonwoven web having a basis weight of 22 g/M² was pattern bonded with a pattern as shown in USD765993 to Palzewicz having a series of spaced large, curvilinear elements. The pattern bonded nonwoven web was then subjected to a CD stretching process utilizing a pair of inter-meshing grooved rolls; the pattern bonded nonwoven web was stretched approximately 2% in the CD. As a result of the CD stretching operation, numerous tears were formed within the individual bond points. An SEM photomicrograph of the CD stretched nonwoven web 200 is shown in FIG. 11 and, as shown therein, the linear bond element 302 has multiple tears 304.

Tests

Tensile Strength: As used herein "tensile strength" or "strip tensile", is the peak load value, i.e. the maximum force produced by a specimen, when it is pulled to rupture. Samples for tensile strength testing are prepared by drying and then die cutting test specimens to a width of 25 mm and length of approximately 152 mm. The instrument used for measuring tensile strengths is an MTS Criterian 42 and MTS TestWorks™ for Windows Ver. 4 (MTS Systems Corp., Research Triangle Park, N.C.). The load cell is selected, depending on the strength of the sample being tested, such that the peak load values fall between 10 and 90 percent of the load cell's full scale load. The gauge length is 76 mm and jaw length is 76 mm. The crosshead speed is 305 mm/minute, and the break sensitivity is set at 70% and the slope preset points at 70 and 157 g. The sample is placed in the jaws of the instrument and centered with the longer dimension parallel to the direction of the load application. The test is then started and ends when the specimen breaks. The peak load is determined, for purposes herein, based upon the CD tensile strength. Six (6) representative specimens are tested, and the arithmetic average of all individual specimen tested is the tensile strength for the product.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of making a nonwoven web comprising:
   directing a fibrous nonwoven spunbond matt in a machine direction, said fibrous nonwoven spunbond matt having a first width in a cross-direction;
   pattern bonding the fibrous nonwoven spunbond matt and forming a pattern bonded nonwoven web, and wherein said pattern comprises (i) discrete individual bond points having a maximum dimension of 1.25 mm or less and an aspect ratio less than 3:1, (ii) macro-elements formed by the individual bond points in a sequent pattern and wherein the macro-elements extend substantially in the machine-direction and have a machine-direction length between about 4 and about 25 mm, (iii) unbonded pockets adjacent the macro-elements having an area between about 20 and about 50 mm², (iv) an overall bond area of between about 5% and about 20%; and
   applying a first stretching force to the pattern bonded nonwoven web in the cross-direction whereby the pattern bonded nonwoven web stretches in the cross direction and has a second width in the cross-direction, the second cross direction width being greater than the first cross direction width; and
   applying a second stretching force to the pattern bonded nonwoven web in the machine direction whereby the pattern bonded nonwoven web necks and has a third width in the cross-direction, the third cross direction width being less than the second cross direction width, and wherein some but less than 2% of the individual bond points are ruptured after both the first and second stretching forces have been applied.

2. The method of claim 1 wherein third cross direction width is at least 0.5% less than the second cross direction width.

3. The method of claim 1 wherein the second cross-direction width is at least 1% greater than the first width.

4. The method of claim 1 wherein the first stretching force is applied by inter-meshing grooved rolls.

5. The method of claim 4 wherein the inter-meshing grooved rolls have a series of ridges and grooves and further wherein the grooved rolls have between 0.25 and 5 ridges per cm.

6. The method of claim 1 wherein the macro-elements are positioned in a plurality of rows extending substantially in the cross direction.

7. The method of claim 6 wherein the macro-elements in adjacent rows are staggered such that macro-elements of an upper row overlay unbonded pockets of the underlying row.

8. The method of claim 1 wherein the spacing between individual bond points forming the macro-elements is between 0.03 and about 0.7 mm.

9. The method of claim 5 wherein the spacing between macro-elements in adjacent rows is between about 0.9 mm and about 2.5 mm.

10. The method of claim 9 wherein the rows overlap in the cross direction.

11. The method of claim 1 wherein less than 1% of the individual bond points are ruptured after both the first and second stretching forces have been applied.

12. The method of claim 1, wherein the fibrous nonwoven spunbond matt is made of fibers having an average diameter of larger than 7 microns.

13. The method of claim 1, wherein less than 0.5% of the individual bond points are ruptured after both the first and second stretching forces have been applied.

* * * * *